US00PP22273P2

(12) United States Plant Patent
Decock

(10) Patent No.: US PP22,273 P2
(45) Date of Patent: Nov. 22, 2011

(54) *LAVANDULA* PLANT NAMED 'EARLY SUMMER'

(50) Latin Name: *Lavandula stoechas*
Varietal Denomination: Early Summer

(75) Inventor: Ludo Decock, Komen (BE)

(73) Assignee: Gartneriet Tvillingegaarden A/S, Odense (DK)

( * ) Notice: Subject to any disclaimer, the term of this patent is extended or adjusted under 35 U.S.C. 154(b) by 0 days.

(21) Appl. No.: 12/927,752

(22) Filed: Nov. 22, 2010

(51) Int. Cl.
*A01H 5/00* (2006.01)

(52) U.S. Cl. ..... Plt./445

(58) Field of Classification Search ..... Plt./445
See application file for complete search history.

*Primary Examiner* — Kent L Bell
(74) *Attorney, Agent, or Firm* — C. A. Whealy

(57) ABSTRACT

A new and distinct cultivar of *Lavandula* plant named 'Early Summer', characterized by its compact, upright and somewhat outwardly spreading plant habit; freely branching growth habit; dense and bushy plant form; early and freely flowering habit; dark violet blue-colored flowers with violet-colored terminal flower bracts; flowers arranged in compact verticillasters on crowded spikes; and good garden performance.

2 Drawing Sheets

Botanical designation: *Lavandula stoechas.*
Cultivar denomination: 'EARLY SUMMER'.

BACKGROUND OF THE INVENTION

The present invention relates to a new and distinct cultivar of *Lavandula* plant, botanically known as *Lavandula stoechas* and hereinafter referred to by the name 'Early Summer'.

The new *Lavandula* plant is a whole plant mutation of *Lavandula stoechas* 'Alexandra', not patented. The new *Lavandula* plant was discovered and selected by the Inventor in 2006 as a single flowering plant within a population of plants of 'Alexandra' in a controlled outdoor nursery environment in Komen, Belgium. The new *Lavandula* was selected on the basis of its compact plant habit and early flowering habit.

Asexual reproduction of the new *Lavandula* by terminal cuttings in a controlled greenhouse environment in Komen, Belgium since 2006 has shown that the unique features of this new *Lavandula* plant are stable and reproduced true to type in successive generations.

SUMMARY OF THE INVENTION

Plants of the new *Lavandula* have not been observed under all possible environmental conditions. The phenotype may vary somewhat with variations in environment such as temperature and light intensity, without, however, any variance in genotype.

The following traits have been repeatedly observed and are determined to be the unique characteristics of 'Early Summer'. These characteristics in combination distinguish 'Early Summer' as a new and distinct cultivar of *Lavandula* plant:

1. Compact, upright and somewhat outwardly spreading plant habit.
2. Freely branching growth habit; dense and bushy plant form.
3. Early and freely flowering habit.

4. Dark violet blue-colored flowers with violet-colored terminal flower bracts; flowers arranged in compact verticillasters on crowded spikes.
5. Good garden performance.

Plants of the new *Lavandula* differ from plants of the parent, 'Alexandra', in the following characteristics:

1. Plants of the new *Lavandula* are more compact than plants of 'Alexandra'.
2. Plants of the new *Lavandula* flower earlier than plants of 'Alexandra'.

Plants of the new *Lavandula* can be compared to plants of *Lavandula stoechas* 'Anouk', disclosed in U.S. Plant Pat. No. 16,685. Plants of the new *Lavandula* differ from plants of 'Anouk' in the following characteristics:

1. Plants of the new *Lavandula* are more compact than plants of 'Anouk'.
2. Plants of the new *Lavandula* flower earlier than plants of 'Anouk'.
3. Plants of the new *Lavandula* and 'Anouk' differ in leaf, flower and terminal flower bract color.
4. Plants of the new *Lavandula* have longer terminal flower bracts than plants of 'Anouk'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph at the top of the first sheet comprises a side perspective view of a typical flowering plant of 'Early Summer' grown in a container.

The photograph at the bottom of the first sheet is a close-up view of a typical flowering stem of 'Early Summer'.

The photograph at the top of the second sheet is a close-up view of a typical inflorescence of 'Early Summer'.

The photograph at the bottom of the second sheet is a close-up view of the upper surface of a typical leaf of 'Early Summer'.

DETAILED BOTANICAL DESCRIPTION

The aforementioned photographs, following observations and measurements describe plants grown during the spring in 11-cm containers in an outdoor nursery in Odense, Denmark and under conditions and practices which approximate those generally used in commercial *Lavandula* production. Plants were 27 weeks old when the photographs and description were taken. During the production of the plants, day temperatures ranged from 15° C. to 27° C. and night temperatures ranged from 3° C. to 15° C. In the following description, color references are made to The Royal Horticultural Society Colour Chart, 2007 Edition, except where general terms of ordinary dictionary significance are used.

Botanical classification: *Lavandula stoechas* 'Early Summer'.

Parentage: Naturally-occurring whole plant mutation of *Lavandula stoechas* 'Alexandra', not patented.

Propagation:

*Type.*—Terminal vegetative cuttings.

*Time to initiate roots, winter.*—About 16 to 18 days at 20° C.

*Root description.*—Fine, fibrous.

Plant description:

*Form.*—Herbaceous perennial; compact, upright and outwardly spreading plant habit; broad inverted triangle.

*Growth habit.*—Moderately vigorous.

*Crop time.*—After rooting, about 20 weeks are required to produce finished flowering plants in 11-cm containers.

*Branching habit.*—Freely branching habit, dense and bushy plant form.

*Plant height.*—About 18 cm.

*Plant width (spread).*—About 20 cm.

*Lateral branch description.*—Length: About 8 cm to 10 cm. Diameter: About 2 mm. Internode length: About 1 cm. Strength: Strong. Aspect: Upright to somewhat outwardly spreading. Texture: Tomentose. Color, immature: Close to 144A. Color, mature: Close to N199A.

*Foliage description.*—Arrangement: Opposite, simple; sessile. Length: About 3 cm. Width: About 4 mm. Shape: Lanceolate. Apex: Acute. Base: Cuneate. Margin: Entire, revolute. Texture, upper and lower surfaces: Pubescent. Fragrance: Aromatic, pungent. Venation pattern: Pinnate. Color: Developing leaves, upper and lower surfaces: Close to 137D. Fully expanded leaves, upper surface: Between N137A and 189A; venation, between N137A and 189A. Fully expanded leaves, lower surface: Between N137A and 189A; venation, close to 137B.

Flower description:

*Flower arrangement and shape.*—Single sessile flowers arranged in compact verticillasters on crowded spikes; freely flowering habit, about nine to ten rows of flowers per verticillaster; flowers salverform with a two-lobed upper lip and a three-lobed lower lip.

*Natural flowering season.*—Long flowering period; flowering continuous from the spring through the summer in Denmark.

*Flower longevity on the plant.*—Longevity of individual flowers is highly dependent on weather conditions; flowers not persistent; terminal flower bracts persistent.

*Fragrance.*—None detected.

*Flower buds.*—Length: About 6 mm. Diameter: About 3 mm. Shape: Oblong. Color: Close to N92C.

*Inflorescence size.*—Height: About 3 cm to 4 cm. Diameter: About 1.3 cm.

*Flowers.*—Diameter: About 4 mm. Depth (height): About 8 mm.

*Petals.*—Lip length: About 1 mm. Lip width: About 1 mm. Lip shape: Roughly spatulate to oval. Lip: Rounded. Lip margin: Entire. Lip texture, upper and lower surfaces: Smooth, glabrous. Lip color: When opening and fully opened, upper surface: Close to N92A. When opening and fully opened, lower surface: Close to N92C.

*Terminal flower bracts.*—Quantity/arrangement: About four in a single whorl at inflorescence apex. Length: About 2 cm to 2.5 cm. Width: About 1 cm. Shape: Oblong to obovate. Apex: Obtuse. Base: Cuneate. Margin: Entire, undulate. Texture, upper and lower surfaces: Pubescent. Color: Immature, upper and lower surfaces: Close to N87C; venation, close to 86B. Mature, upper and lower surfaces: Close to 86B; venation, close to 86B.

*Flower bracts.*—Arrangement: Each whorl of flowers subtended by a flower bract. Length: About 7 mm. Width: About 8 mm. Shape: Broadly ovate. Apex: Broadly acute. Base: Cuneate. Margin: Entire. Texture, upper surface: Tomentose. Texture, lower surface: Smooth, glabrous. Color, immature and mature, upper surface: Close to 146A tinted with close to N187B; towards the base, close to 144A; venation, close to 147A. Color, immature and mature, lower surface: Close to 146A; venation, close to 147A.

*Sepals.*—Arrangement: Five sepals fused into a campanulate tube. Length: About 5 mm. Width: About 1 mm to 2 mm. Shape: Lanceolate. Apex: Four have acute apexes; the apex of the fifth sepal is rounded. Margin: Entire. Texture, upper surface: Tomentose. Texture, lower surface: Smooth, glabrous. Color, immature and mature, upper surface: Close to 146A tinted with close to N187B; towards the base, close to 144D. Color, immature and mature, lower surface: Close to 144B.

*Peduncles.*—Length: About 4 cm to 6 cm. Diameter: About 2 mm. Strength: Strong. Aspect: Mostly upright. Color: Close to 143A.

*Reproductive organs.*—Stamens: Quantity per flower: Four. Filament length: About 1 mm. Anther shape: Reniform. Anther length: About 0.5 mm. Pollen amount: Scarce. Pollen color: Yellow. Pistils: Quantity per flower: One. Pistil length: About 5 mm. Stigma shape: Club-shaped. Stigma color: Dark purple. Style length: About 4 mm. Style color: Whitish. Ovary color: Yellow green.

*Seeds.*—Length: About 2 mm. Diameter: About 2 mm.

Disease/pest resistance: Plants of the new *Lavandula* have not been noted to be resistant to pathogens and pests common to *Lavandula*.

Garden performance: Plants of the new *Lavandula* have exhibited good tolerance to rain and wind and hardy to USDA Hardiness Zone 7.

It is claimed:

1. A new and distinct *Lavandula* plant named 'Early Summer' as illustrated and described.

* * * * *

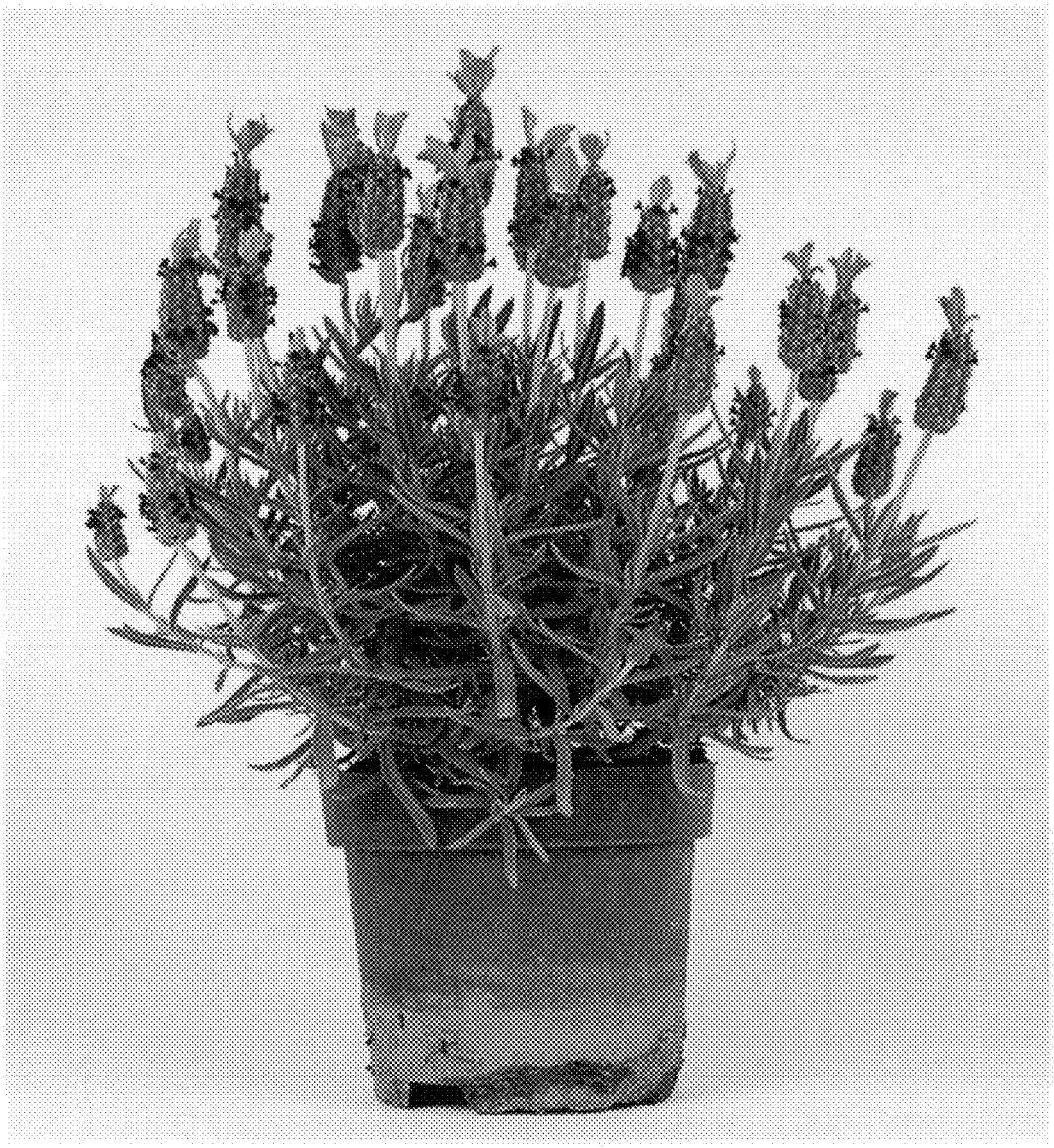
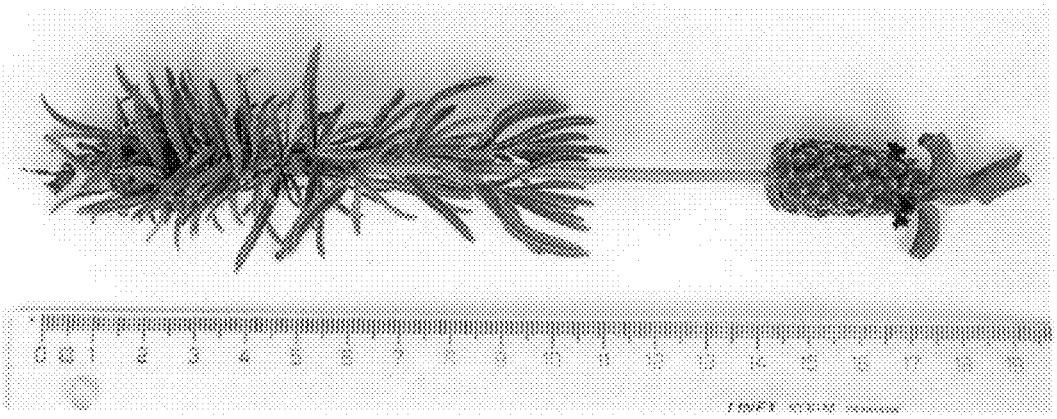

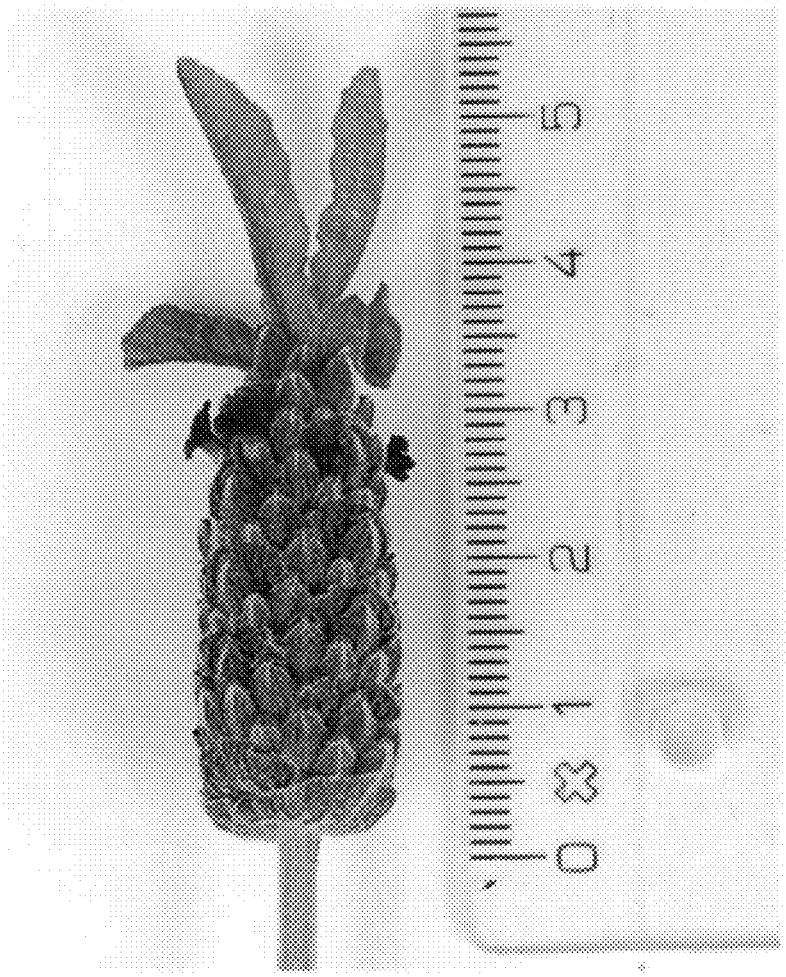
0
1
2
3
4
5
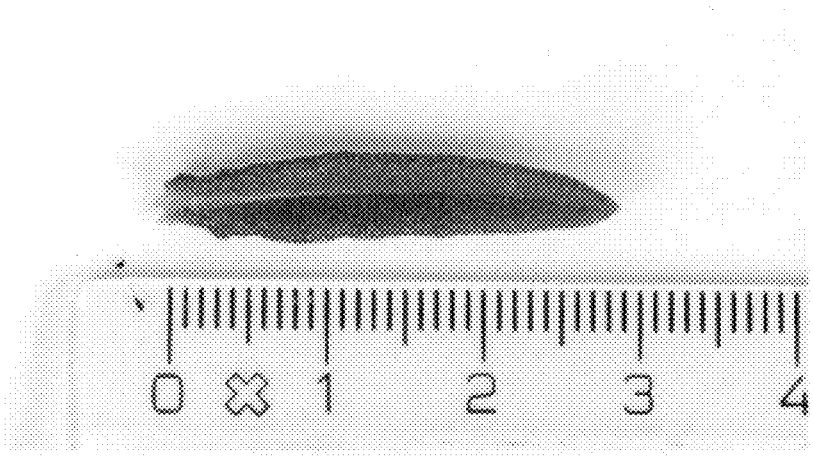
0
1
2
3
4